United States Patent

Kirby et al.

Patent Number: 5,252,949
Date of Patent: Oct. 12, 1993

[54] CHEMICAL SENSOR FOR CARBON MONOXIDE DETECTION

[75] Inventors: Kevin W. Kirby, Malibu; Hiroshi Kimura, Northridge; Ricardo C. Pastor, Manhattan Beach, all of Calif.

[73] Assignee: Hughes Aircraft Company, Los Angeles, Calif.

[21] Appl. No.: 751,029

[22] Filed: Aug. 28, 1991

[51] Int. Cl.$^5$ .............................. G08B 17/10
[52] U.S. Cl. ................... 340/632; 73/23.31; 340/633
[58] Field of Search ................. 340/632–634; 324/693; 73/23.31–23.32

[56] References Cited

U.S. PATENT DOCUMENTS 4,968,656  11/1990  Fukuda et al. .................. 502/244

FOREIGN PATENT DOCUMENTS

| 1076948 | 4/1986 | Japan | 73/23.31 |
| 150849 | 6/1986 | Japan | 73/23.31 |
| 2021259 | 1/1990 | Japan | 73/23.31 |
| 2149122 | 6/1985 | United Kingdom | 324/693 |

Primary Examiner—Thomas Mullen
Attorney, Agent, or Firm—V. D. Duraiswamy; W. K. Denson-Low

[57] ABSTRACT

A ceramic sensor (12) comprising a thin film (14) of $Cu_{1-x}Mn_{2-x}O_{4-y}$ is provided that quantitatively measures the partial pressure of CO gas in a flowing system (22). The sensor is specific to CO gas and is negligibly affected by the presence of the common automobile exhaust vapors NO, $H_2O$, and $CH_4$, within the operational temperature range from about 250° to 450° C. The CO sensor of the invention has other applications, such as monitoring CO levels in laboratories, mines, and industrial smoke stacks, and may be used in environments up to about 700° C.

11 Claims, 6 Drawing Sheets

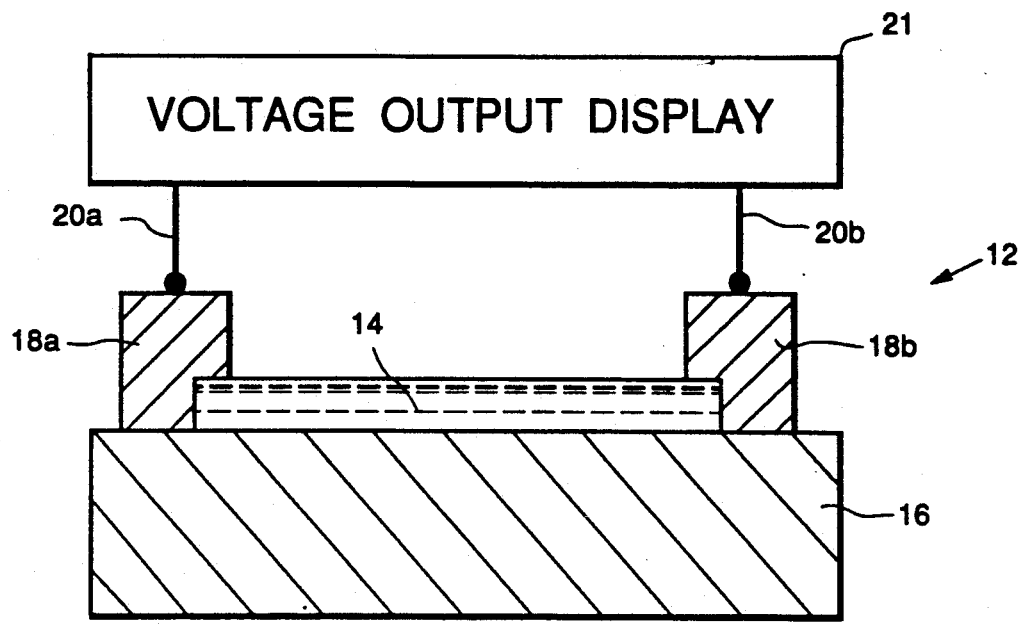
FIG. 2.
FIG. 3.
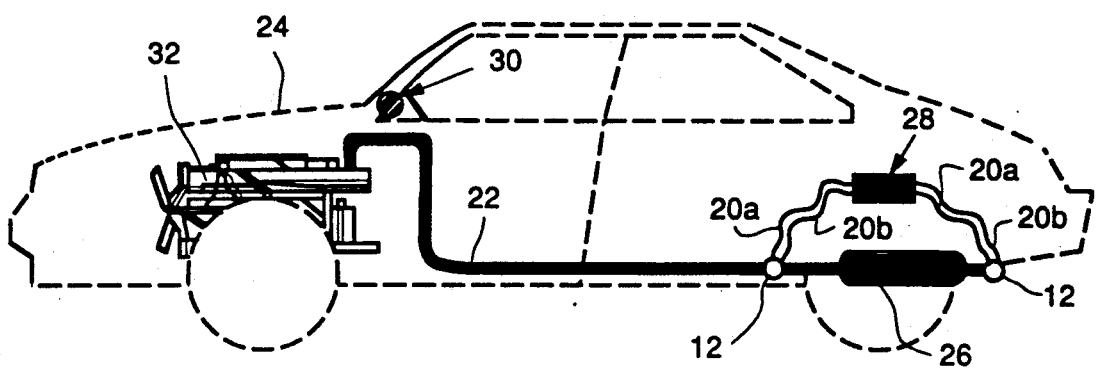

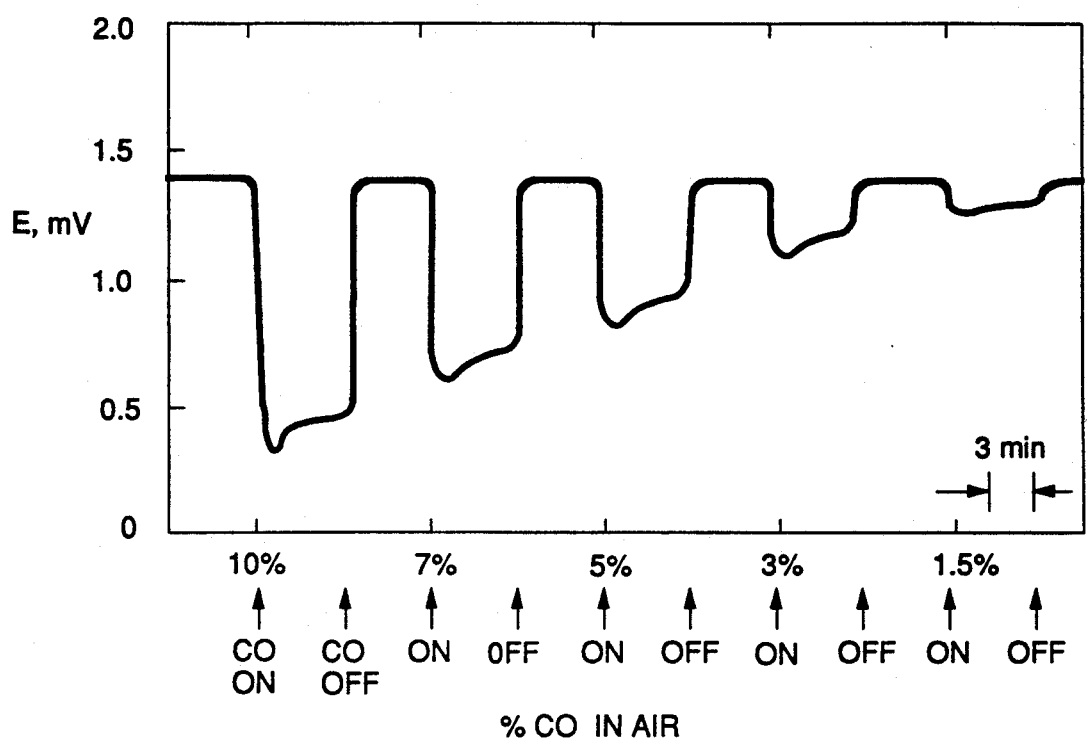
FIG. 4.
FIG. 5.
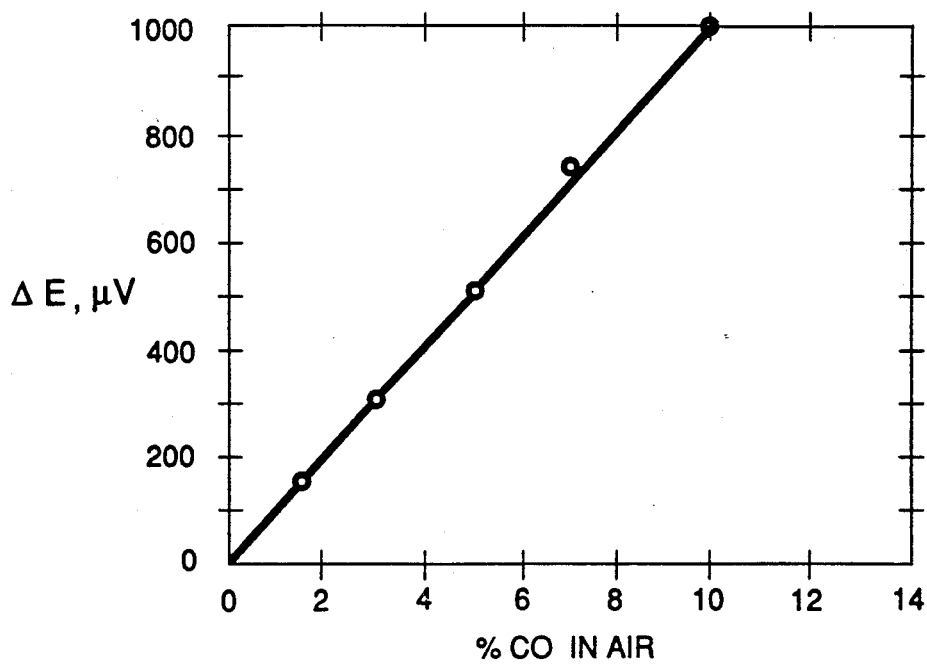

CHEMICAL SENSOR FOR CARBON MONOXIDE DETECTION

BACKGROUND OF THE INVENTION

1. Field of the Invention

The present invention relates to detection of automobile exhausts, and, more particularly, to the detection of carbon monoxide gas in the presence of other gases.

2. Description of Related Art

A sensor for CO gas has immediate application to automobiles for monitoring catalytic converter efficiency. Sensors placed before and after the catalytic converter would be able to quantitatively monitor the oxidation efficiency of environmentally harmful CO by the converter. Another automobile application includes real-time control of engine processes via a feedback loop of exhaust composition from a strategically located sensor.

A secondary application is for CO monitoring in a general sense. This could include the quantitative determination of CO present in fuel cells, or a simple detection of CO in laboratories, mines, and industrial smoke stacks.

Semiconductive metal oxides have been used as CO and hydrocarbon sensors. Two major problems are encountered, however. The first is a non-linearity in the signal response when the mixture of oxidizable gas and oxygen reaches a stoichiometric ratio for combustion. For the case of CO, this occurs when the $CO/O_2$ ratio equals 2:1 in the following reaction:

$$2CO + O_2 = 2 CO_2. \quad (1)$$

When this ratio is attained, the signal can change by over an order of magnitude, and the calibration of sensor is therefore lost.

The second problem encountered with metal oxide sensors is a lack of detection specificity with respect to an individual gas in a gas mixture. This can be a particular problem in the case of automobile exhaust, where signal interference can arise from the presence of NO(g), $H_2O$ vapor, and other hydrocarbon gases resulting from fuel combustion.

Thus, there is a need for a CO sensor that is substantially free of the problems of the prior art sensors.

SUMMARY OF THE INVENTION

In accordance with the invention, a ceramic sensor is provided that quantitatively measures the partial pressure of CO gas in a flowing system. The sensor is specific to CO gas and is negligibly affected by the presence of the common automobile exhaust vapors NO, $H_2O$, and $CH_4$, within the operational temperature range from about 250° to 450° C.

The sensor of the invention comprises a defect copper manganese oxide, $Cu_{1+x}Mn_{2-x}O_{4-y}$, having the spinel structure. While one sensor might be used in a particular application, a pair of sensors is desirably employed in connection with the monitoring of CO gas in automobile exhaust, one placed before the catalytic converter and one after.

The sensor of the invention comprises a thin film of the copper manganese oxide, supported on a substrate, to which metal contact is made so as to measure any change in surface resistance during exposure to CO in the exhaust gas stream. Such a change in resistance is a measure of the quantity of CO.

For automotive use, a comparator logic means accepts the input of the two CO sensors, compares the two inputs, and sends a signal to the driver if the CO level from the exhaust exceeds a certain pre-set level. Alternatively, the signal may be used to control the air/fuel mixture in the engine to enhance combustion efficiency and hence the performance of the automobile.

Experiments at different ratios of $CO/O_2$, including the stoichiometric ratio in Eqn. 1, have shown that the sensor of the invention does not exhibit the non-linear signal response of the prior art sensors, and therefore can quantitatively measure CO concentration over an appreciable range.

Further, the sensor of the invention is insignificantly affected by the presence of other combustion by-products in the detection of CO at the levels encountered in actual automobile exhausts.

BRIEF DESCRIPTION OF THE DRAWINGS

FIG. 2 is a cross-sectional view of the CO sensor of the invention;

FIG. 3 is a schematic diagram depicting one use of the CO sensor of the invention;

FIG. 4, on coordinates of potential (in mV) and CO concentration (% in air), is a plot of signal response of the $CuMn_2O_4$ sensor of the invention at varying CO concentrations in air;

FIG. 5, on coordinates of change in potential (in $\mu V$) and CO concentration (% in air) is a calibration plot of the voltage change with concentration of CO in air;

DESCRIPTION OF THE PREFERRED EMBODIMENTS

Figure 1A:
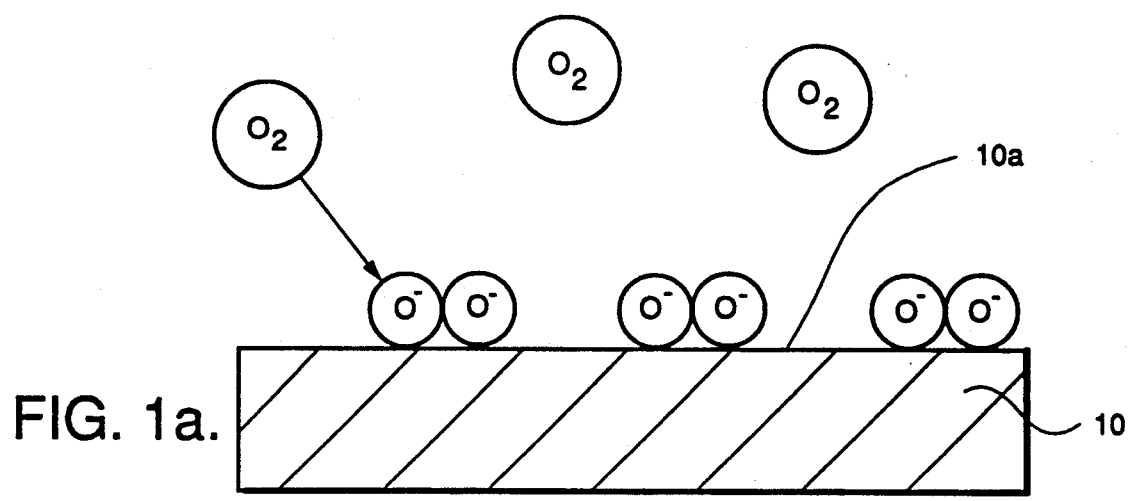
FIGS. 1a–c are a schematic representation of what is believed to be occurring on the surface of the CO sensor of the invention.

A ceramic sensor has been developed that quantitatively measures the partial pressure of CO gas in a flowing system. The sensor is specific to CO gas and is negligibly affected by the presence of the common automobile exhaust vapors NO, $H_2O$, and $CH_4$ within the operational temperature range of about 250° to 450° C. and within the compositional range encountered in automobile exhaust.

The sensor of the invention has been made in thin film form easily and inexpensively from a metallo-organic deposition (MOD) process. The MOD process consists of dissolving together organic salts of the metal constituents into a solution which is then deposited onto the surface of an appropriate substrate. Examples of materials employed as appropriate substrates include insulating materials, such as oxides (alumina, magnesia, zirconia, etc). Deposition techniques include spray, dip, or spin coating of the solution. The deposited solution is then dried and heated at temperatures of at least about 800° C. to form the crystalline ceramic oxide. Films with thicknesses up to 1 μm and greater may be fabricated.

A sensor test structure includes a film produced by this or other deposition technology on a suitable substrate, and a 4-point array of metal contacts on the film surface. Metal contacts such as gold have been evaporated onto film surfaces, with the desired pattern easily produced by masking. Leads from the metal contact connect to current generating and resistance measuring circuitry to provide electrical evaluation of the sensor.

The ceramic sensor of the invention has the ability to determine levels of CO gas emanating from automobile combustion, without the detrimental effects encountered from other combustion by-products, as indicated above. Since the sensor of the invention comprises a ceramic material, it is able to operate at relatively high temperatures with minimum degradation of integrity.

The sensor of the invention employs $CuMn_2O_4$, which has a spinel structure and can be easily prepared in bulk form by solid state reaction of $CuO$ and $Mn_3O_4$ at 900° C. The resulting material is actually slightly Cu-rich and can be better described by the formula $Cu_{1=x}Mn_{2-x}O_{4-y}$, where x ranges from 0 to about 0.5, and preferably is at least about 0.05, and y ranges from 0 to about 0.25. This latter compound is a defect version of the parent compound, with the extra Cu cations occupying the octahedral Mn sites in the spinel structure. This type of behavior is well-documented for a variety of spinel-type oxides, and contributes to the semiconductive behavior observed in this material and ultimately to the material's sensor capability.

The principle of operation relies on the chemisorption and subsequent reaction of gaseous species on the sensor surface. For the case of detecting CO in a gaseous mixture having a partial pressure of oxygen [P(O$_2$) finite], both CO and O$_2$ molecules are attracted to the sensor surface and undergo chemisorption. Reaction of these molecules at the surface via Eqn. 1 with subsequent desorption of the resulting CO$_2$ molecule establishes an equilibrium at the surface with respect to the concentration of chemisorbed molecules. Assuming that CO$_2$ formation (Eqn. 1) proceeds more slowly than the chemisorption process, then the concentration of CO and O$_2$ molecules on the surface becomes a function of their respective partial pressures in the gas mixture. Molecules of CO are reducing and tend to donate electrons during chemisorption, while O$_2$ molecules ionize to O$^{n-}$, thereby removing electrons from the surface. It is this balance that dictates the free carrier population on the sensor surface and therefore the surface resistance. As this balance changes due to the partial pressure change of CO in the gas mixture, there is a corresponding change in the surface resistance of the sensor, providing the basis for a signal response.

Figure 1B:
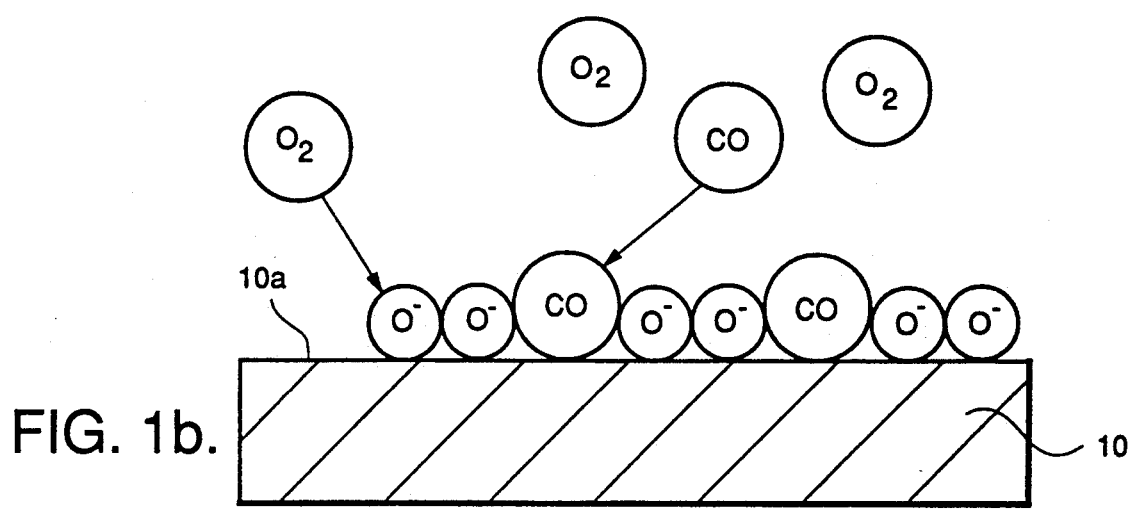
Figure 1C:
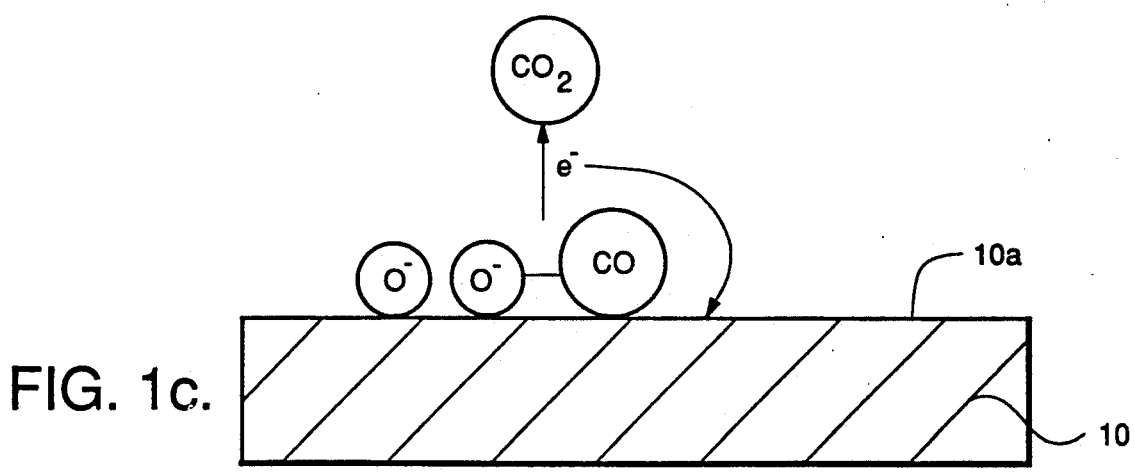

Without subscribing to any particular theory, a model is presented in FIGS. 1a-c, which illustrates material changes in the sensor due to the presence of carbon monoxide and is the basis for the quantitative detection of this gas. As shown in FIG. 1a, in the presence of a partial pressure of oxygen [P(O$_2$) finite], a surface 10a of a sample 10 attracts oxygen in a chemisorption process, forming oxygen anions (O$^{n-}$). FIG. 1a depicts this process, showing O$^-$ anions on the sample surface 10a. The corresponding equation relating to chemisorption is given by

$$2e^- + O_2 \xrightarrow{k_2} 2O^-. \qquad (2)$$

It will be observed that for this process to occur, electrons must be provided from the sample 10. The presence of oxygen in this form on the surface of oxides and non-oxides is well-established and represents the state of the sensor of the invention at time zero (in other words, this is the normal state of the sensor in the presence of only oxygen or air).

The introduction of CO gas into the sensor ambient results in a similar covering of the sensor surface 10a at available sites, as shown in FIG. 1b. Although CO tends to be an electron donating species, i.e., reducing, it may be assumed that the molecule remains neutrally charged on the surface 10a. The rate equation depicting the adsorption of CO is

$$CO(g) \xrightarrow{k_3} CO(ads). \qquad (3)$$

In the event that CO and O$^-$ come in close proximity as in FIG. 1c, a reaction between the two may occur, whereby CO$_2$ gas is formed, and an electron is released to the sample 10. This process is shown by Eqn. (4):

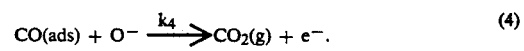

$$CO(ads) + O^- \xrightarrow{k_4} CO_2(g) + e^-. \qquad (4)$$

This electron contributes to the overall charge carrier population at the sample surface 10a and therefore the sample resistance. The initial state has an abundance of O$^-$ on the sample surface 10a, making the rate k$_4$ of Eqn. (4) solely dependent upon the concentration of CO adsorbed. One can therefore obtain a value for the relative concentration of CO gas in the ambient by measuring changes in the surface resistance.

The sensor 12 of the invention is depicted in FIG. 2. A thin film 14 of the metal oxide is formed on a substrate 16. Metal contacts 18a, 18b at two separate points (here, the ends of the film 14) are used to measure the resistance of the thin film. Corresponding leads 20a, 20b provide an output, such as to means 2a for relating the change in surface resistance to the quantity of CO. A conventional 4-point probe (not shown) may alternately be employed, as described elsewhere herein.

In one embodiment, depicted in FIG. 3, two such sensors 12 are placed in the exhaust pipe 22 of an automobile 24, one prior to the catalytic converter 26, and one after. The leads 20a, 20b are routed to a comparator logic means 28, which compares the two inputs, and sends a signal to the driver by means of a dash warning light 30 if the CO level from the exhaust exceeds a certain pre-set level. Alternatively, the signal may be used to control the air/fuel mixture in the engine 32, for better combustion efficiency. Such adjustment may be made as the level of CO increases, for example.

To increase the potential lifetime of the sensor 12 of the invention, a gas sampling scheme has been developed such that the sensor is not continuously exposed to the corrosive environment of the automobile exhaust. Instead, the sensor 12 is located in a separate sampling chamber (not shown) connected to the main exhaust line 22. At regular intervals, a small amount of the exhaust gas is allowed to enter the sensor chamber for sampling and quantitative CO determination. Sampling intervals may vary from seconds to minutes, depending on the driving conditions and type of automobile.

Quantitative determination of CO is most accurate when the sensor remains isothermal. A small resistance heater embedded in the substrate surface 16 beneath the film 14 in conjunction with a thermocouple (not shown) would increase the thermal stability of the sensor, and thus the detection accuracy.

In a series of tests, the surface resistance was measured with a conventional 4-point DC probe technique with output to a strip chart recorder. Changes in current-voltage characteristics correspond to changes in the sample surface resistivity. The sensitivity of the measurement was in the 1,000 ppm range. The temperature range of operation was from about 200° to 500° C., compatible with engine exhaust temperatures. However, the range of operation of the sensor of the invention is not so limited, and may be operated in environments up to about 700° C.; this is to be compared with most prior art CO sensors, which are limited to temperatures ranging no higher than about 400° to 500° C.

FIG. 4 shows the signal response of the sensor at varying concentrations of CO in air [P(O$_2$) 0.2 atm] at 430° C. Signal drift can be attributed to flowmeter instability. When plotting the data from FIG. 4 as voltage change vs. CO concentration in the gas mixture, a linear response is observed, as seen in FIG. 5. The concentration of CO in the gas mixture can therefore be evaluated from the sensor signal and the calibration plot of FIG. 5.

As indicated above, a major problem encountered by conventional metal oxide CO sensors is the signal non-linearity when the CO/O$_2$ ratio equals 2:1. The data obtained so far approach the 2:1 point and reveal no signal non-linearity or step function change in resistance. This behavior correlates with a sample surface that is only slightly catalytically active with respect to the reaction of Eqn. 1.

Figure 6:
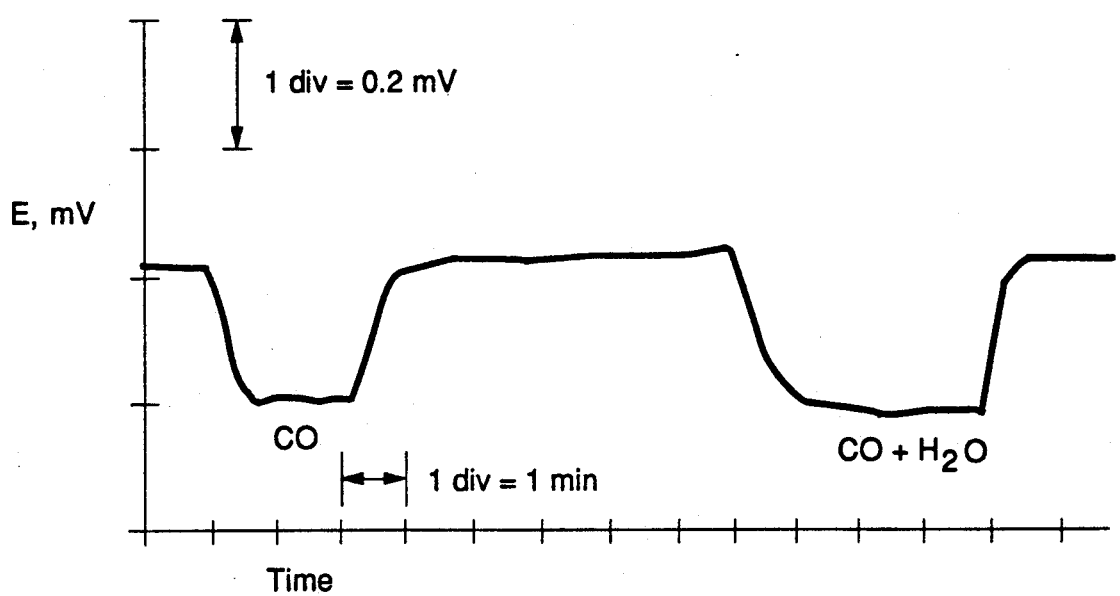
FIG. 6, on coordinates of potential (in mV) and time, is a plot of the effect of water vapor on the signal response of the sensor of the invention from 5% CO in air at a temperature of about 350° C.

The effect of other gases on sensor performance is a critical parameter that was evaluated with H$_2$O, NO, and CH$_4$ gases or vapors. FIG. 6 shows the signal for air with 5.0 vol.% CO at about 350° C. and the effect of this same gas mixture saturated with H$_2$O at room temperature ($\approx$3% H$_2$O by volume). The signal strength remained unchanged by the presence of H$_2$O carried on CO. The apparent increase in response time is an artifact of the flow-mixing system used to introduce the H$_2$O vapor into the CO gas stream.

Figure 7:
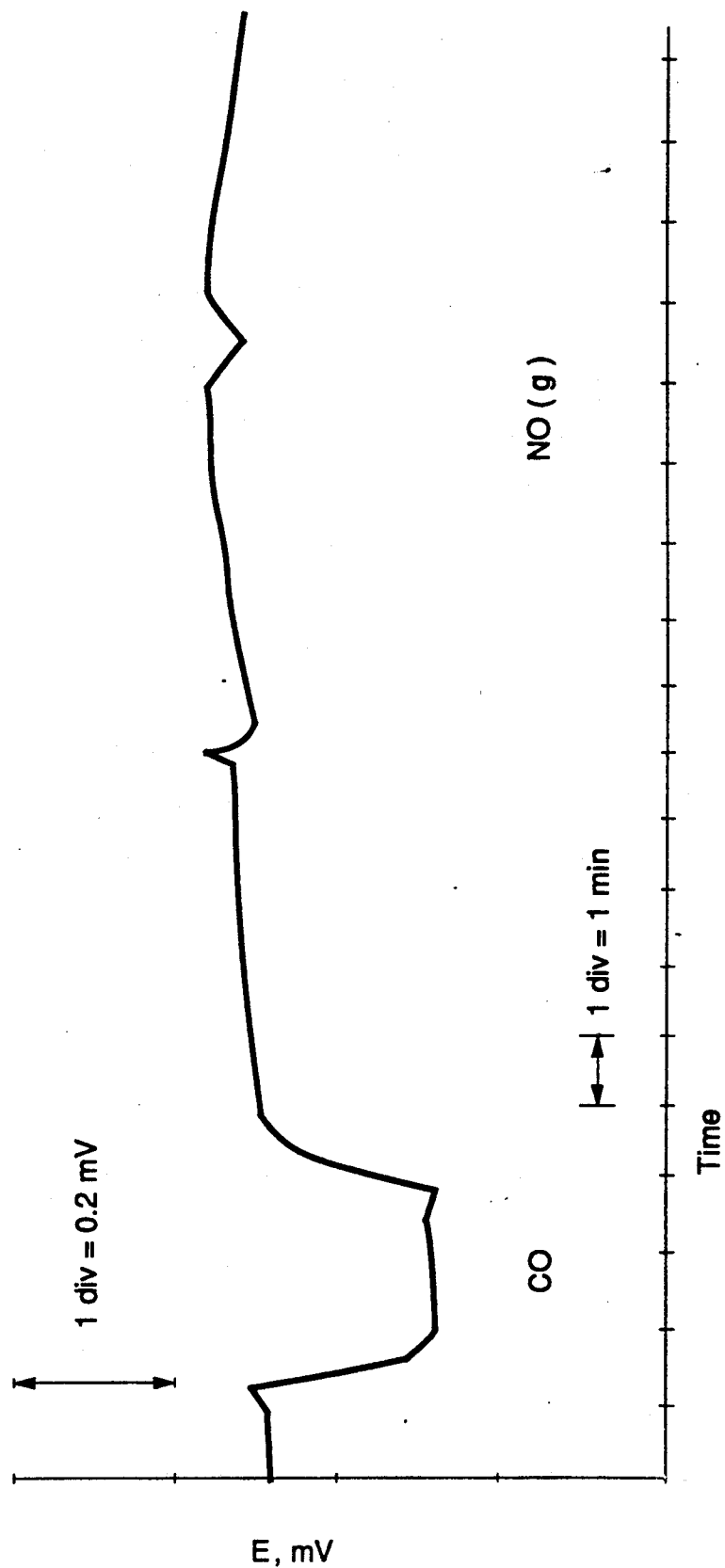
FIG. 7 is a plot similar to that of FIG. 6, showing the effect of NO(g) on the sensor of the invention at about 350° C.

The effect of NO(g) was evaluated similarly at the same temperature. FIG. 7 shows the sensor response to the addition of 1.0 vol.% NO to air. The spikes represent the cooling and heating effects from the change in total flow when turning on and off the NO gas. In fact, the small shift in baseline has been found to be due to the cooling effect from the increase in flow rate. The quantity of NO exposed to the sensor in these experiments was about five to ten times higher than that encountered in automobile exhaust.

Figure 8:
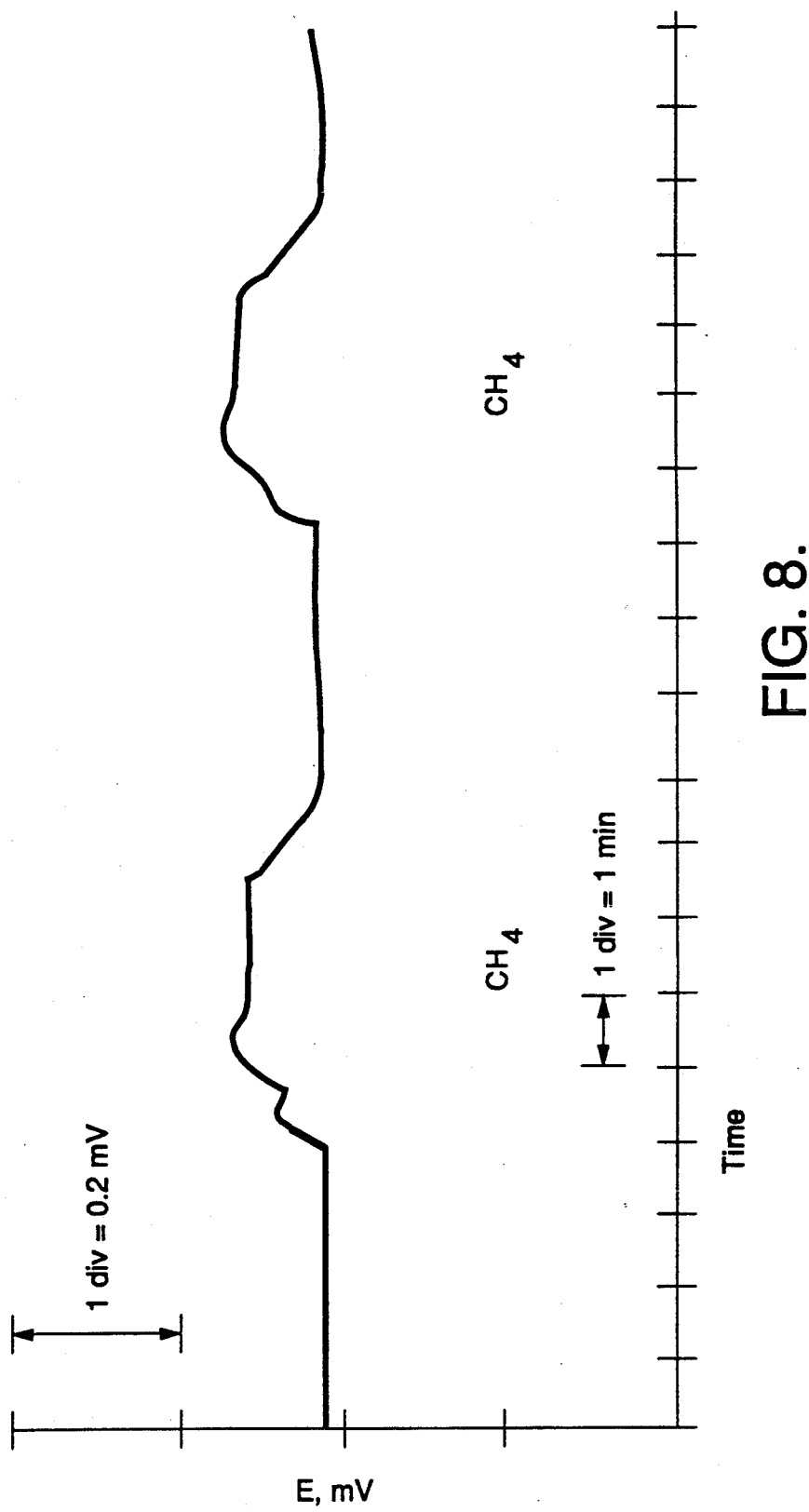
FIG. 8 is a plot similar to that of FIG. 6, showing the effect of $CH_4(g)$ on the sensor of the invention at about 350° C.

Hydrocarbon effects on CO detection were examined with methane gas (CH$_4$) at 350° C. The major effect of an 11.0 vol.% CH$_4$ addition was again sample cooling, as seen in FIG. 8. Some contribution from the methane molecule to the observed signal is likely, but remains an insignificant factor, since the total hydrocarbon concentration in automobile exhaust is $\leq$5,000 ppm. The CH$_4$ study was performed twice (without the CO standard) to show reproducibility of curve shape.

Thus, there has been disclosed a sensor for detecting CO, such as in automobile exhausts. It will be appreciated that various changes and modifications of an obvious nature may be made without departing from the spirit of the invention, and all such changes and modifications are considered to fall within the scope of the invention as defined by the appended claims.

What is claimed is:

1. A sensor for detecting CO in a flowing gas stream comprising:
   (a) a surface layer comprising Cu$_{1+x}$Mn$_{2-x}$O$_{4-y}$, said surface layer having a surface layer resistance which changes as a function of CO concentration;
   (b) means for measuring said surface layer resistance on said surface layer;
   (c) means for determining any difference between said measured surface layer resistance in the absence of said flowing gas stream at said surface layer and in the presence of said flowing gas stream at said surface layer; and
   (d) means for relating said difference to CO concentration in said flowing gas stream.

2. The sensor of claim 1 wherein said surface layer resistance is determined by measuring the resistance of said surface layer between at least two separated contact points.

3. The sensor of claim 1 wherein x ranges from 0 to about 0.5 and wherein y ranges from 0 to about 0.25.

4. The sensor of claim 3 wherein x is at least about 0.05.

5. A CO detector system for detecting CO in a flowing gas stream passing through a catalytic converter comprising:
   (a) two CO sensors, one sensor located upstream of said catalytic converter and the other sensor located downstream of said catalytic converter, each CO sensor comprising
      (1) a surface layer comprising Cu$_{1+x}$Mn$_{2-x}$O$_{4-y}$, supported on a substrate, aid surface layer having a surface layer resistance which changes as a function of CO concentration on aid surface layer and
      (2) means for measuring the surface layer resistance of said surface layer;
   (b) comparator means to receive said measured surface layer resistance from each CO sensor and to compare said measured resistances; and
   (c) output means to provide a warning signal if the difference between said measured resistances exceeds a pre-set limit or to make adjustments in engine air/fuel ratio.

6. The detector system of claim 5 wherein said surface layer resistance is determined by measuring the resistance of said surface layer between at least two separated contact points.

7. The detector system of claim 5 wherein x ranges from 0 to 0.5 and wherein y ranges from 0 to about 0.25.

8. The detector system of claim 7 wherein is at least about 0.05.

9. A method for measuring the CO concentration in a flowing gas stream comprising:
   (a) causing said gas stream to flow over a surface comprising Cu$_{1+x}$Mn$_{2-x}$O$_{4-y}$, said surface layer having a surface layer resistance which changes as a function of CO concentration on said surface layer;
   (b) measuring said surface layer resistance on said surface layer;
   (c) determining any difference between said measured surface layer resistance in the absence of said flowing gas stream at said surface layer and in the presence of said flowing gas stream at said surface layer; and (d) relating said difference to CO concentration in said flowing gas stream.

10. The method of claim 9 wherein x ranges from 0 to about 0.5 and wherein y ranges from 0 to about 0.25.

11. The method of claim 10 wherein x is at least about 0.05.

* * * * *